United States Patent [19]

Brooker et al.

[11] 3,976,661

[45] Aug. 24, 1976

[54] PYRROLO HEMIOXONOL DYES

[75] Inventors: Leslie G. S. Brooker, Rochester;
Arthur Fumia, Jr., Hilton; Donald W. Heseltine, Rochester, all of N.Y.

[73] Assignee: Eastman Kodak Company, Rochester, N.Y.

[22] Filed: Jan. 18, 1974

[21] Appl. No.: 434,751

Related U.S. Application Data

[62] Division of Ser. No. 201,571, Nov. 23, 1971, Pat. No. 3,813,397, which is a division of Ser. No. 56,657, July 20, 1970, Pat. No. 3,652,289.

[52] U.S. Cl. .................. 260/326.5 SF; 260/326.35; 260/326.36; 260/326.43; 260/326.5 J; 260/326.62; 260/326.82

[51] Int. Cl.² .............. C07D 295/14; C07D 405/08; C07D 409/08

[58] Field of Search ................. 260/326.62, 326.43, 260/326.5 J, 326.82, 326.5 SF

[56] References Cited
UNITED STATES PATENTS

| | | | |
|---|---|---|---|
| 3,449,368 | 6/1969 | Shen et al. | 260/326.35 |
| 3,717,629 | 2/1973 | Maier et al. | 260/244 |

*Primary Examiner*—Nicholas S. Rizzo
*Assistant Examiner*—David E. Wheeler
*Attorney, Agent, or Firm*—J. G. Levitt

[57] ABSTRACT

Novel trimethine hemioxonol dyes are provided in which the polymethine chain of the dye includes the 1, 2 and 3 carbon atoms of a 1-cyclohexen-3-ylidene nucleus, the 1-carbon atom of said 1-cyclohexen-3-ylidene nucleus having the nitrogen atom of a tertiary amino group attached thereto. Photographic emulsions and elements are also provided featuring the trimethine hemioxonol dyes of the invention as spectral sensitizers or as filter material.

2 Claims, No Drawings

PYRROLO HEMIOXONOL DYES

This is a division of application Ser. No. 201,581, filed Nov. 23, 1971 now U.S. Pat. No. 3,813,397, issued May 28, 1974, which in turn is a division of U.S. Ser. No. 56,657 filed July 20, 1970 now U.S. Pat. No. 3,652,289 issued Mar. 28, 1972.

This invention relates to novel photographic materials, and more particularly to a new class of rigidized hemioxonol dyes, to filter layers and light-sensitive photographic silver halide emulsions and elements prepared therewith, and to the preparation of these novel dyes and photographic materials.

It is known that hemioxonol dyes spectrally sensitize light-sensitive silver halide emulsions, and are useful as light-screening substances in photographic elements. Light-screening substances are often required (a) in backing layers on either side of the support to reduce halation, (b) in overcoats on photographic elements to protect the light-sensitive emulsion or emulsions from the effects of ultraviolet light, particularly in the case of color photographic elements, and (c) in interlayers between differentially color-sensitized emulsions to protect an underlying emulsion layer or layers from unwanted action of certain wavelengths of light. However, many of the hemioxonol dyes that have been employed as light-screening materials are relatively unstable on exposure to ultraviolet radiation or do not have sufficiently sharp absorption maxima and high extinction coefficients in the desired regions of the spectrum.

It is, accordingly, an object of this invention to provide hemioxonol spectral sensitizing and filter dyes.

Another object of this invention is to provide photographic silver halide emulsions containing one or more of the hemioxonol dyes of the invention.

Still another object of this invention is to provide filter layers comprising one or more of the hemioxonol dyes of the invention.

A further object of this invention is to provide means for preparing the new dyes and novel photographic materials of the invention.

Other objects of this invention will be apparent from this disclosure and the appended claims.

In one embodiment of this invention, trimethine hemioxonol dyes are provided in which the polymethine chain of the dye includes the 1,2 and 3 carbon atoms of a 1-cyclohexen-3-ylidene nucleus, the 1-carbon atom of said 1-cyclohexen-3-ylidene nucleus having the nitrogen atom of a tertiary amino group attached thereto.

In another embodiment of this invention, trimethine hemioxonol dyes are provided in which the polymethine chain of the dye includes the 1,2 and 3 carbon atoms of a 1-cyclohexen-3-ylidene nucleus, the 1-carbon atom of said 1-cyclohexen-3-ylidene nucleus having attached thereto a substituent selected from the group consisting of a pyrrolidyl group, a 4-alkyl-1-piperazinyl group, a 4-alkoxycarbonyl-1-piperazinyl group, a piperidyl group and a morpholinyl group.

The 1,2 and 3 carbon atoms of a 1-cyclohexen-3-ylidene nucleus are indicated in the following structural formula:

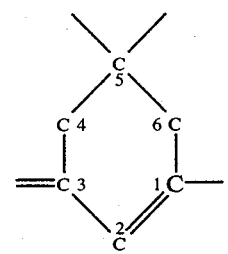

The preferred dye compounds of this invention include those represented by the following formulas:

I.
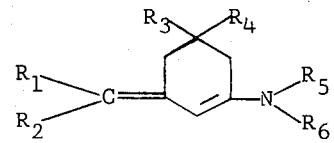

and

II.
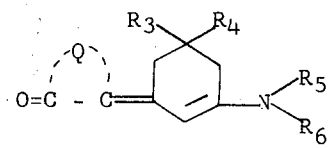

wherein $R_1$ and $R_2$ each represents the same or different member such as a cyano group, an alkoxycarbonyl group, preferably containing from 1 to 4 carbon atoms in the alkoxy group, e.g., methoxycarbonyl, ethoxycarbonyl, propoxycarbonyl, isopropoxycarbonyl, butoxycarbonyl, etc., acyl, preferably containing from 2 to 5 carbon atoms, such as acetyl, propionyl and butyryl, or cyclic acyl groups such as benzoyl, furoyl and thenoyl

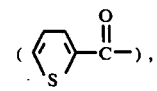

or, an arylsulfonyl group, such as phenylsulfonyl or naphthyl sulfonyl, an alkylsulfonyl group, preferably containing from 1 to 4 carbon atoms, e.g., methylsulfonyl, ethylsulfonyl, propylsulfonyl, isopropylsulfonyl, butylsulfonyl, etc., or, an aryloxysulfonyl group, such as phenoxysulfonyl, provided not more than one of $R_1$ and $R_2$ represents an alkylsulfonyl group or an arylsulfonyl group; $R_3$ and $R_4$ each represents a hydrogen atom or a lower alkyl group containing from 1 to 4 carbon atoms, e.g., methyl, ethyl, propyl, isoporpyl, butyl, etc.; $R_5$ and $R_6$, taken separately, represent an alkyl group, preferably of from 1 to 4 carbon atoms, such as methyl, ethyl, propyl, or butyl, or an aryl group, preferably a mononuclear aryl group, e.g., phenyl or tolyl, and taken together, $R_5$ and $R_6$ represent the nonmetallic atoms necessary to complete a heterocyclic nucleus having from 5 to 6 atoms in the heterocyclic ring such as, for example, a pyrrolidyl group, a 4-alkyl-1-piperazinyl group in which the alkyl group preferably contains from 1 to 4 carbon atoms, e.g., 4-methyl-1-piperazinyl or 4-butyl-1-piperazinyl, a 4-alkoxycarbonyl-1-piperazinyl group in which the alkoxy group preferably contains from 1 to 4 carbon atoms, e.g., a 4-ethoxycarbonyl-1-piperazinyl group; a thiamorpholinyl group, an indoline ring, a decahydroquinoline ring, etc., a piperidyl group or a morpholinyl group; and Q represents the non-metallic atoms necessary to complete a 5- or 6-membered nitrogen containing heterocyclic ketomethylene nucleus of the type used in merocyanine dyes such as a 2-pyrazolin-5-one nucleus, e.g., 3-methyl-1-phenyl-2-pyrazolin-5-one, 1-phenyl-2-pyrazolin-5-one, 1-(2-benzothiazolyl)-3-methyl-2-pyrazolin-5-one, etc.; an isoxazolone nucleus, e.g., 3-phenyl-5(4H)-isoxazolone, 3-methyl-5(4H)-isoxazolone, etc.; an oxindole nucleus, e.g., 1-alkyl-2-oxindoles, etc.; a 2,4,6-triketohexahydropyrimidine nucleus, e.g., barbituric acid or 2-thiobarbituric acid as well as their 1-alkyl (e.g., 1-methyl, 1-ethyl, 1-propyl, 1-heptyl, etc.) or 1,3-dialkyl (e.g., 1,3-dimethyl, 1,3-diethyl, 1,3-dipropyl, 1,3-diisopropyl, 1,3-dicyclohexyl, 1,3-di($\beta$-methoxyethyl), etc.; or, 1,3-diaryl (e.g., 1,3-diphenyl, 1,3-di-(p-chlorophenyl),1,3-di(p-ethoxycarbonylphenyl), etc.); or 1-aryl (e.g., 1-phenyl, 1-p-chlorophenyl, 1-p-ethoxycarbonylphenyl), etc.) or 1-alkyl-3-aryl (e.g., 1-ethyl-3-phenyl, 1-n-heptyl-3-phenyl, etc.) derivatives; a rhodanine nucleus (e.g., 2-thio-2,4-thiazolidinedione series), such as rhodanine, 3-alkylrhodanines, e.g., 3-ethylrhodanine, 3-allylrhodanine, etc., 3-carboxyalkylrhodanines, e.g., 3-(2-carboxyethyl)rhodanine, 3-(4-carboxybutyl)rhodanine, etc., 3-sulfoalkylrhodanines, e.g., 3-(2-sulfoethyl)rhodanine, 3-(3-sulfopropyl)rhodanine, 3-(4-sulfobutyl)-rhodanine, etc., or 3-arylrhodanines, e.g., 3-phenylrhodanine, etc., etc.; a 2(3H)-imidazo[1,2-a]pyridone nucleus; a 5,7-dioxo-6,7-dihydro-5-thiazolo[3,2-a]pyrimidine nucleus, e.g., 5,7-dioxo-3-phenyl-6,7-dihydro-5-thiazolo[3,2-a]pyrimidine, etc.; a 2-thio-2,4-oxazolidinedione nucleus (i.e., those of the 2-thio-2,4(3H,5H)-oxazoledione series) e.g., 3-ethyl-2-thio-2,4-oxazolidinedione, 3-(2-sulfoethyl)-2-thio-2,4-oxazolidinedione, 3-(4-sulfobutyl)-2-thio-2,4-oxazolidinedione, 3-(3-carboxypropyl)-2-thio-2,4-oxazolidinedione, etc.; a thianaphthenone nucleus, e.g., 3-(2H)-thianaphthenone, etc.; a 2-thio-2,5-thiazolidinedione nucleus (i.e., the 2-thio-2,5-(3H,4H)-thiazoledione series), e.g., 3-ethyl-2-thio-2,5-thiazolidinedione, etc.; a 2,4-thiazolidinedione nucleus, e.g., 2,4-thiazolidinedione, 3-ethyl-2,4-thiazolidinedione, 3-phenyl-2,4-thiazolidinedione, 3-$\alpha$-naphthyl-2,4-thiazolidinedione, etc.; a thiazolidinone nucleus, e.g., 4-thiazolidinone, 3-ethyl-4-thiazolidinone 3-phenyl-4-thiazolidinone, 3-$\alpha$-naphthyl-4-thiazolidinone, etc.; a 2-thiazolin-4-one nucleus, e.g., 2-ethylmercapto-2-thiazolin-4-one, 2-alkylphenylamino-2-thiazolin-4-one, 2-diphenylamino-2-thiazoline-4-one, etc.; a 2-imino-4-oxazolidinone (i.e., pseudohydantoin) nucleus; a 2,4-imidazolidinedione (hydantoin) nucleus, e.g., 2,4-imidazolidinedione, 3-ethyl-2,4-imidazolidinedione, 3-phenyl-2,4-imidazolidinedione, 3-$\alpha$-naphthyl-2,4-imidazolidinedione, 1,3-diethyl-2,4-imidazolidinedione, 1-ethyl-3-phenyl-2,4-imidazolidinedione, 1-ethyl-3-$\alpha$-naphthyl-2,4-imidazolidinedione, 1,3-diphenyl-2,4-imidazolidinedione, etc.; a 2-thio-2,4-imidazolidinedione (i.e., 2-thiohydantoin) nucleus, e.g., 2-thio-2,4-imidazolidinedione, 3-ethyl-2-thio-2,4-imidazolidinedione, 3-(4-sulfobutyl)-2-thio-2,4-imidazolidinedione, 3-(2-carboxyethyl)-2-thio-2,4-imidazolidinedione, 3-phenyl-2-thio-2,4-imidazolidinedione, 3-$\alpha$-naphthyl-2-thio-2,4-imidazolidinedione, 1,3-diethyl-2-thio-2,4-imidazolidinedione, 1-ethyl-3-phenyl-2-thio-2,4-imidazolidinedione, 1-ethyl-3-$\alpha$-naphthyl-2-thio-2,4-imidazolidinedione, 1,3-diphenyl-2-thio-2,4-imidazolidinedione, etc.; a 2-imidazolin-5-one nucleus, e.g., 2-propylmercapto-2-imidazolin-5-one, etc.; etc. The dyes defined by Formula I above are primarily useful as filter dyes, while those defined by Formula II above are primarily useful as spectral sensitizing dyes.

The trimethine hemioxonol dyes of this invention are outstanding filter dyes and spectral sensitizers for light sensitive silver halide. These dyes have excellent light stability which renders them highly useful as ultraviolet filter dyes. In addition, these new dyes have extinction coefficients in the range of 6 to 8 × 10$^4$, which is higher than most prior art filter dyes. Hence, lower concentrations of the dyes of this invention are required than related dyes of the prior art. Dyes of this invention which absorb in the blue region of the spectrum, i.e., those having maximum absorption peaks greater than 400 nm., are also powerful spectral sensitizers for silver halide emulsions.

The term "trimethine hemioxonols" is used herein to include dyes that are (1)derived from an $\alpha$-ketomethylene compound of the type used in the preparation of merocyanine dyes, (2) contain an amino methylene group and (3) contain three methine groups. See Hamer, *The Cyanine Dyes and Related Compounds*, published by Interscience Publishers, 1964, pages 465 and 486. Note that dyes such as those of Example 1 are considered to be trimethine hemioxonols, even though they do not contain a carbonyl group, because such dyes contain two acidic nuclei joined by three methine groups.

In accordance with another embodiment of this invention, trimethine hemioxonol dyes can be prepared by heating a quaternary salt of a 3-chlorocyclohex-2-en-1-ylidene compound having substituted on the 1-carbon atom thereof the nitrogen atom of a tertiary amino group with an acidic compound having an active methylene group of the type used in the preparation of hemioxonol dyes, in the presence of a basic condensing agent. Preferably the nitrogen atom of the tertiary amino group is in a heterocyclic ring containing from 5 to 6 atoms.

The dye compounds embraced by Formula I above are prepared by condensing an intermediate (1) of the formula:

III.

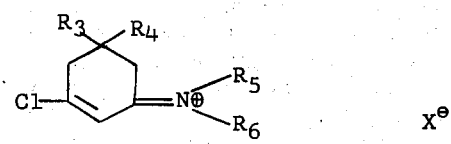

wherein $R_3$, $R_4$, $R_5$ and $R_6$ are as previously defined and X represents any acid anion, e.g., chloride, bromide, iodide, perchlorate, p-toluenesulfonate, methyl sulfate, etc., with (2) a compound of the formula:

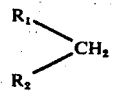

III.

wherein $R_1$ and $R_2$ are as previously defined, in approximately equimolar proportions, in suitable solvent medium, e.g., an alkanol such as methanol, ethanol, etc., at elevated temperatures and preferably at refluxing temperatures of the reaction mixtures, in the presence of a basic condensing agent such as a trialkylamine, e.g., triethylamine, tri-n-butylamine, etc., N-methylpiperidine, N-ethylpiperidine, N,N-dimethylaniline, etc. The dye compounds are then separated from the reaction mixtures by chilling, the crude crystals collected and washed, followed by one or more recrystallizations from suitable solvents such as methanol and mixtures of solvents, for example, pyridine/methanol and pyridine/chloroform.

The dye compounds embraced by Formula II above are prepared in general similar condensation conditions except that (1) a compound of Formula III above is condensed with a (2) heterocyclic ketomethylene compound having the following formula:

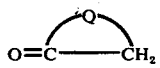

V.

wherein Q is as previously defined.

The intermediate compounds defined by Formula III above are prepared in accordance with the method described by Alt and Speziale, J. Org. Chem., 29, 794–797 (1964).

In the preparation of non-photographic filter layers coated on a transparent support; or photographic filter layers between differentially sensitized emulsion layers; filter layers on diffusion transfer receiving sheets such as those described in Land U.S. Pat. No. 2,543,181, Feb. 27, 1951; filter layers in or upon color print materials such as those described in VanCampen U.S. Pat. No. 2,956,879, issued Oct. 18, 1960; filter layers in or upon color transfer materials such as those described in British Pat. No. 890,861, dated Mar. 7, 1962, Belgian Pat. No. 636,371, and Rogers U.S. Pat. No. 3,087,817, issued Apr. 30, 1963 and U.S. Pat. No. 2,983,606, issued May 9, 1961; and the like; the dyes of this invention are preferably incorporated in colloid layers which can contain silver halide, and are permeable to aqueous processing solutions, said dyes being employed in concentrations which may vary considerably depending upon the particular product concerned and the effect desired. Suitable support materials for the filter layers include those conventional in the photographic art such as paper, glass, metals, cellulose acetate, cellulose acetate-propionate, polystyrene, polyesters, polyvinyl chloride, polypropylene, etc. Methods for selecting the particular colloid to be employed, and for determining the amount of dye to be included, are well known in the art and need not be enumerated here. Representative colloids which may be employed include natural materials such as gelatin, protein derivatives, albumin, agar-agar, gum arabic, alginic acid and the like; and synthetic resins such as polyvinyl alcohol, polyvinyl pyrrolidone, polyacrylamide, cellulose ethers and carboxylated derivatives of cellulose ethers, partially hydrolyzed cellulose esters, copolymers of acrylic and methacrylic acids, polymeric latexes or hydrosols, mixtures of these, and the like. Gelatin is the preferred colloid.

The concentration of the new dyes in the emulsion can vary widely, e.g., from about 5 to about 100 mg. per liter of flowable emulsion. The specific concentration will vary according to the type of light-sensitive material in the emulsion and the effects desired. The suitable and most economical concentration for a given emulsion will be apparent to those skilled in the art upon making the tests and observations customarily used in the art of emulsion making. With most of the dyes, 10 to 20 mg. of dye per liter of emulsion suffices to produce the maximum sensitizing effect with the ordinary gelatin-silver bromide (including bromoiododide and chlorobromide) emulsions. With fine grain emulsions, which include most of the ordinarily employed gelatin-silver chloride emulsions, somewhat larger concentrations of dye may be necessary to obtain the optimum sensitizing effect.

Silver halide emulsions spectrally sensitized by the dyes of this invention can comprise silver chloride, silver bromide, silver bromoiodide, silver chlorobromoiododide or mixtures thereof. Such emulsions can be coarse, medium or fine grain (or mixtures thereof) and can be prepared by any of the well-known procedures, e.g., single jet emulsions, double jet emulsions. Useful emulsions include Lippmann emulsions, ammoniacal emulsions, thiocyanate or thioether ripened emulsions such as those described in Nietz et al. U.S. Pat. No. 2,222,264, Illingsworth U.S. Pat. No. 3,320,069, and McBride U.S. Pat. No. 3,271,157; or, cubic grain emulsions, such as those described by Kline and Moisar, Journal of Photographic Science, volume 12, page 242 et seq., or Markocki, The Spectral Sensitization of Silver Bromide Emulsions on Different Crystallographic Faces, Journal of Photographic Science, volume 13, 1965. Surface image emulsions can be used or internal image emulsions such as those described in Davey et al. U.S. Pat. No. 2,592,250; Lowe et al. U.S. Pat. No. 3,206,313; Berriman et al. U.S. Pat. No. 3,367,778 and Bacon et al. Belgian Pat. No. 704,255. If desired, mixtures of surface and internal image emulsions can be used as described in Luckey et al. U.S. Pat. No. 2,996,382. Negative type emulsions can be used as well as direct positive emulsions such as those described in Leermakers U.S. Pat. No. 2,184,013; Kendall et al. U.S. Pat. No. 2,541,472; Berriman U.S. Pat. No. 3,367,778; Schouivenaars British Patent 723,019; Illingsworth French Pat. No. 1,520,821; Ives U.S. Pat. No. 2,563,785; Knott et al. U.S. Pat. No. 2,456,953 and Land U.S. Pat. No. 2,861,885.

The silver halide emulsions spectrally sensitized with the dyes of this invention can be unwashed or washed to remove soluble salts. In the latter case the soluble salts can be removed by chill-setting and leaching or the emulsion can be coagulation washed, e.g., by the procedures described in Hewitson et al U.S. Pat. No. 2,618,556; Yutzy et al. U.S. Pat. No. 2,614,928; Yackel U.S. Pat. No. 2,565,418; Hart et al. U.S. Pat. No. 3,241,969; and Waller et al. U.S. Pat. No. 2,489,341.

Photographic emulsions containing a dye in accordance with this invention can be sensitized with chemical sensitizers, such as with reducing agents; sulfur, selenium or tellurium compounds; gold, platinum or palladium compounds; or combinations of these. Suitable chemical sensitization procedures are described in Shepard U.s. Pat. No. 1,623,499; Allen U.S. Pat. No. 2,399,083; McVeigh U.S. Pat. No. 3,297,447; and Dunn U.S. Pat. No. 3,297,446.

The spectrally sensitized silver halide emulsions of this invention can contain speed increasing compounds such as polyalkylene glycols, cationic surface active agents and thioethers or combinations of these as described in Piper U.S. Pat. No. 2,886,437; Chechak U.S.

Pat. No. 3,046,134; Carroll et al. U.S. Pat. No. 2,944,900; and Goffe U.S. Pat. No. 3,294,540.

Silver halide emulsions containing a dye of this invention can be protected against the production of fog and can be stabilized against loss of sensitivity during keeping. Suitable antifoggants and stabilizers, which can be used alone or in combination, include the thiazolium salts described in Staud U.S. Pat. No. 2,131,038 and Allen U.S. Pat. No. 2,694,716; the azaindenes described in Piper U.S. Pat. No. 2,886,437 and Heimbach U.S. Pat. No. 2,444,605; the mercury salts described in Allen U.S. Pat. No. 2,728,663; the urazoles described in Anderson U.S. Pat. No. 3,287,135; the sulfocatechols described in Kennard U.S. Pat. No. 3,236,652; the oximes described in Carroll et al. British Patent No. 623,448; nitron; nitroindazoles; the mercaptotetrazoles described in Kendall et al. U.S. Pat. No. 2,403,927; Kennard et al. U.S. Pat. No. 3,266,897 and Luckey et al. U.S. Pat. No. 3,397,987; the polyvalent metal salts described in Jones U.S. Pat. No. 2,839,405; the thiuronium salts described in Herz U.S. Pat. No. 3,220,839; and the palladium, platinum and gold salts described in Trivelli U.S. Pat. No. 2,566,263 and Damschroder U.S. Pat. No. 2,597,915.

Photographic elements including emulsions spectrally sensitized in accordance with this invention can contain incorporated developing agents such as hydroquinones, catechols, aminophenols, 3-pyrazolidones, ascorbic acid and its derivatives, reductones and phenylenediamines, or combinations of developing agents. The developing agents can be in a silver halide emulsion and/or in another suitable location in the photographic element. The developing agents can be added from suitable solvents or in the form of dispersions as described in Yackel U.S. Pat. No. 2,592,368 and Dunn et al. French Patent No. 1,505,778.

Silver halide spectrally sensitized in accordance with the invention can be dispersed in colloids that can be hardened by various organic or inorganic hardeners, alone or in combination, such as the aldehydes, and blocked aldehydes, ketones, carboxylic and carbonic acid derivatives, sulfonate esters sulfonyl halides and vinyl sulfones, active halogen compounds, epoxy compounds, aziridines, active olefins, isocyanates, carbodiimides, mixed function hardeners and polymeric hardeners such as oxidized polysaccharides, e.g., dialdehyde starch, oxyguargum, etc.

Photographic emulsions spectrally sensitized with a dye of this invention can contain various colloids alone or in combination as vehicles or binding agents. Suitable hydrophilic materials include both naturally-occurring substances such as proteins, for example, gelatin, gelatin derivatives, cellulose derivatives, polysaccharides such as dextran, gum arabic and the like; and synthetic polymeric substances such as water soluble polyvinyl compounds, e.g., poly(vinylpyrrolidone) acrylamide polymers or other synthetic polymeric compounds such as dispersed vinyl compounds in latex form, and particularly those which increase the dimensional stability of the photographic materials. Suitable synthetic polymers include those described, for example, in U.S. Pat. No. 3,142,568 of Nottorf, issued July 28, 1964; U.S. Pat. No. 3,193,386 of White, issued July 6, 1965; U.S. Pat. No. 3,062,674 of Houck, Smith and Yudelson, issued Nov. 6, 1962; U.S. Pat. No. 3,220,844 of Houck, Smith and Yudelson, issued Nov. 30, 1965; Ream and Fowler U.S. Pat. No. 3,287,289, issued Nov. 22, 1966; and Dykstra U.S. Pat. No. 3,411,911; particularly effective are those water-insoluble polymers of alkyl acrylates and methacrylates, acrylic acid, sulfoalkyl acrylates or methacrylates, those which have cross linking sites which facilitate hardening or curing and those having recurring sulfobetaine units as described in Canadian patent No. 744,054.

Emulsions spectrally sensitized in accordance with this invention can be used in photographic elements which contain antistatic or conducting layers, such as layers that comprise soluble salts, e.g., chlorides, nitrates, etc., evaporated metal layers, ionic polymers such as those described in Minsk U.S. Pat. Nos. 2,861,056 and 3,206,312 or insoluble inorganic salts such as those described in Trevoy U.S. Pat. No. 3,428,451.

Photographic emulsions containing a dye of this invention can be coated on a wide variety of supports. Typical supports include cellulose nitrate film, cellulose ester film, poly(vinyl acetal) film, polystyrene film, poly(ethylene terephthalate) film, polycarbonate film and related films or resinous materials, as well as glass, paper, metal and the like. Typically, a flexible support is employed, especially a paper support, which can be partially acetylated or coated with baryta and/or an alpha-olefin polymer, particularly a polymer of an alpha-olefin containing 2 to 10 carbon atoms such as polyethylene, polypropylene, ethylene-butene copolymers and the like.

Spectrally sensitized emulsions of the invention can contain plasticizers and lubricants such as polyalcohols, e.g., glycerin and diols of the type described in Milton U.S. Pat. No. 2,960,404; fatty acids or esters such as those described in Robijns U.S. Pat. No. 2,588,765 and Duane U.S. Pat. No. 3,121,060; and silicone resins such as those described in DuPont British Patent No. 955,061.

The photographic emulsions spectrally sensitized as described herein can contain surfactants such as saponin, anionic compounds such as the alkyl aryl sulfonates described in Baldsiefen U.S. Pat. No. 2,600,831 and amphoteric compounds such as those described in Ben-Ezra U.S. Pat. No. 3,133,816.

Photographic elements containing emulsion layers sensitized as described herein can contain matting agents such as starch, titanium dioxide, zinc oxide, silica polymeric beads including beads of the type described in Jelley et al U.S. Pat. No. 2,992,101 and Lynn U.S. Pat. No. 2,701,245.

Spectrally sensitized emulsions of the invention can be utilized in photographic elements which contain brightening agents including stilbene, triazine, oxazole and coumarin brightening agents. Water soluble brightening agents can be used such as those described in Albers et al. German Patent No. 972,067 and McFall et al. U.S. Pat. No. 2,933,390 or dispersions of brighteners can be used such as those described in Jansen German Patent No. 1,150,274 and Oetiker et al. U.S. Pat. No. 3,406,070.

Light sensitive photographic emulsion layers spectrally sensitized with the subject dye combinations can be used in photographic elements which contain light absorbing materials and filter dyes such as those described in Sawdey U.S. Pat. No. 3,253,921; Gaspar U.S. Pat. No. 2,274,782; Carroll et al. U.S. Pat. No. 2,527,583 and Van Campen U.S. Pat. No. 2,956,879. If desired, the dyes can be mordanted, for example, as described in Milton and Jones U.S. Pat. No. 3,282,699.

The sensitizing dyes (and other emulsion addenda) can be added to the photographic emulsion from water solutions or suitable organic solvent solutions, for example with the procedure described in Collins et al. U.S. Pat. No. 2,912,343; Owens et al. U.S. Pat. No. 3,342,605; Audran U.S. Pat. No. 2,996,287 or Johnson et al. U.S. Pat. No. 3,425,835. The dyes of this invention can be dispersed in a hydrophilic colloid and the dispersion of dye in the colloid can be added to a dispersion of silver halide in hydrophilic colloid, to spectrally sensitize the silver halide, as described in Owens et al. U.S. Pat. No. 3,465,736 issued Sept. 30, 1969.

Photographic emulsions of this invention can be coated by various coating procedures including dip coating, air knife coating, curtain coating, or extrusion coating using hoppers of the type described in Beguin U.S. Pat. No. 2,681,294. If desired, two or more layers may be coated simultaneously by the procedures described in Russell U.S. Pat. No. 2,761,791 and Wynn British Pat. No. 837,095.

Emulsions spectrally sensitized as described herein are useful in colloid transfer processes such as described in Yackel et al. U.S. Pat. No. 2,716,059; silver salt diffusion transfer processes such as described in Rott U.S. Pat. No. 2,352,014, Land U.S. Pat. No. 2,543,181, Yackel U.S. Pat. No. 3,020,155 and Land U.S. Pat. No. 2,861,885; color image transfer processes such as described in Rogers U.S. Pat. Nos. 3,087,817; 3,185,567; and 2,983,606; Weyerts U.S. Pat. No. 3,253,915, Whitmore et al. U.S. Pat. Nos. 3,227,550; 3,227,551 and 3,227,552; and Land U.S. Pat. Nos. 3,415,644; 3,415,645; 3,415,646; and imbibition transfer processes as described in Minsk U.S. Pat. No. 2,882,156.

Photographic emulsions of this invention can be used in elements designed for recording print out images as described in Fallesen U.S. Pat. No. 2,369,449 or Bacon et al. Belgian Pat. No. 704,255; direct print images as described in Hunt U.S. Pat. No. 3,033,682 and McBride U.S. Pat. No. 3,287,137; elements designed for processing by heat as described in Sorensen et al. U.S. Pat. No. 3,152,904, 3M British Patent No. 1,110,046, Stewart U.S. Pat. No. 3,312,550 and Colt U.S. Pat. No. 3,148,122; or, in elements designed for physical development such as those described in Agfa British Pat. No. 920,277 and Gilman et al. British Pat. No. 1,131,238.

Silver halide emulsions containing the dyes of this invention can be used in elements designed for color photography, for example, elements containing color-forming couplers such as those described in Frolich et al. U.S. Pat. No. 2,376,679; Vittum et al. U.S. Pat. No. 2,322,027; Fierke et al. U.S. Pat. No. 2,801,171; Godowsky U.S. Pat. No. 2,698,794; Barr et al. U.S. Pat. No. 3,227,554 and Graham U.S. Pat. No. 3,046,129; or elements to be developed in solutions containing color-forming couplers such as those described in Mannes and Godowsky U.S. Pat. No. 2,252,718; Carroll et al. U.S. Pat. No. 2,592,243 and Schwan U.S. Pat. No. 2,950,970.

Exposed photographic emulsions of this invention can be processed by various methods including processing in alkaline solutions containing conventional developing agents such as hydroquinones, catechols, aminophenols, 3-pyrazolidones, phenylenediamines, ascorbic acid derivatives, hydroxylamines, hydrazines and the like; web processing such as described in Tregillus et al. U.S. pat. No. 3,179,517; stabilization processing as described in Yackel et al. "Stabilization Processing of Films and Papers," *PSA Journal*, Vol. 16B, August, 1950; monobath processing as described in Levy "Combined Development and Fixation of Photographic Images with Monobaths, " *Phot. Sci. and Eng.*, Vol. 2, No. 3, Oct. 1958, and Barnes et al. U.S. Pat. No. 3,392,019. If desired, the photographic emulsions of this invention can be processed in hardening developers such as those described in Allen et al U.S. Pat. No. 3,232,761; in roller transport processors such as those described in Russell U.s. Pat. No. 3,025,779; or by surface application processing as described in Example 3 of Kitze U.S. Pat. No. 3,418,132.

The silver halide emulsions spectrally sensitized by the dyes of this invention can be used for making lithographic printing plates such as by the colloid transfer of undeveloped and unhardened areas of an exposed and developed emulsion to a suitable support as described in Clark et al. U.S. Pat. No. 2,763,553; to provide a relief image as described in Woodward U.S. Pat. No. 3,402,045 or Spencer U.S. Pat. No. 3,053,658; or, to prepare a relief printing plate as described in Baxter et al. U.S. Pat. No. 2,271,150.

Photographic silver halide emulsions spectrally sensitized with a dye described herein can contain other spectral sensitizing dyes, such as other dyes of the type described herein or, for example, one or more of the dyes described in Brooker and White U.S. Pat. No. 2,526,632, issued Oct. 24, 1950; Sprague U.S. Pat. No. 2,503,776, issued Apr. 11, 1950; Brooker et al. U.S. Pat. No. 2,493,748; and Taber et al. U.S. Pat. No. 3,384,486. Other spectral sensitizing dyes which can be used in combination with the dyes of this invention include the cyanine, merocyanines, complex (tri or tetranuclear) merocyanines, complex (tri or tetranuclear) cyanines, holopolar cyanines, styryls, hemicyanines (e.g. enamine hemicyanines), oxonols and hemioxonols. Dyes of the cyanine classes may contain such basic nuclei as the thiazolines, oxazolines, pyrrolines, pyridines, oxazoles, thiazoles, selenazoles and imidazoles. Such nuclei may contain alkyl, alkylene, hydroxyalkyl, sulfoalkyl, carboxyalkyl, aminoalkyl, and enamine groups and may be fused to carbocyclic or heterocyclic ring systems either unsubstituted or substituted with halogen, phenyl, alkyl, haloalkyl, cyano, or alkoxy groups. The dyes may be symmetrical or unsymmetrical and may contain alkyl, phenyl, enamine or heterocyclic substituents on the methine or polymethine chain. The merocyanine dyes may contain the basic nuclei mentioned above as well as acid nuclei such as thiohydantoins, rhodanines, oxazolidenediones, thiazolidenediones, barbituric acids, thiazolineones, and malononitrile. These acid nuclei may be substituted with alkyl, alkylene, phenyl, carboxyalkyl, sulfoalkyl, hydroxyalkyl, alkoxyalkyl, alkylamino groups, or heterocyclic nuclei. Combinations of these dyes may be used, if desired. In addition, supersensitizing addenda which do not absorb visible light may be included; for instance, ascorbic acid derivatives, azaindenes, cadmium salts, and organic sulfonic acids, as described in McFall et al. U.S. Pat. No. 2,933,390 and Jones et al. U.S. Pat. No. 2,937,089.

The invention is further illustrated by the following examples.

EXAMPLE 1

[5,5-Dimethyl-1-(1-pyrrolidinyl)-1-cyclohexen-3-ylidene] malonitrile

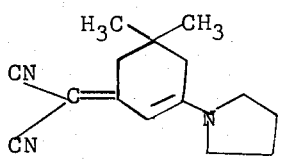

N-(3-Chloro-5,5-dimethylcyclohex-2-en-1-ylidene)-pyrrolidiniumperchlorate (9.4 g., 0.03 mol.) and malononitrile (2.0 g., 0.03 mol.) are dissolved in warm ethanol (25 ml.). Triethylamine (4.6 ml.) is then added and a vigorous reaction takes place with a solid precipitating. The mixture is then heated at reflux for 5 minutes. After chilling, the crude dye is collected on a filter and rinsed with ethanol and dried. After one recrystallization from methanol, the yield of purified dye is 3.0 g. (83%), m.p. 246°–247°C. This purified dye is an excellent light-absorbing dye in photographic layers as shown in the absorption data in Table 1 hereinafter.

EXAMPLE 2

Decyl-[5,5-dimethyl-1-(1-pyrrolidinyl)-1-cyclohexen-3-ylidene] cyanoacetate

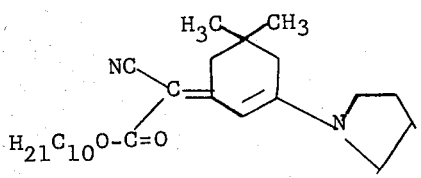

N-(3-Chloro-5,5-dimethylcyclohex-2-en-1-ylidene)-pyrrolidinium perchlorate (9.4 g.), decylcyanoacetate (6.8 g.) and triethylamine (4.6 ml.) are dissolved in ethanol (15 ml.) and heated at reflux for 5 minutes. After cooling at room temperature for several minutes, a pasty solid separates and methanol (75 ml.) is added. After chilling, the crude product is collected on a filter, rinsed with ethanol and dried. After one recrystallization from methanol the yield of purified dye is 3.8 g. (63%), m.p. 122°–123°C. This dye shows excellent absorption in the ultraviolet to blue region of the spectrum and is a useful filter dye in photographic elements. The absorption characteristics of this dye are shown in Table 1 hereinafter.

EXAMPLE 3

3-Ethyl-5-[5,5-dimethyl-1-(1-pyrrolidinyl)-1-cyclohexen-3-ylidene]rhodanine

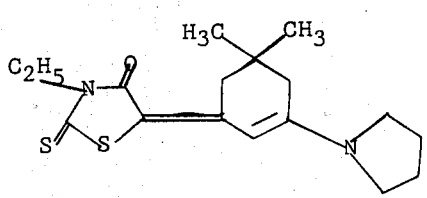

N-(3-Chloro-5,5-dimethylcyclohex-2-en-1-ylidene)-pyrrolidinium perchlorate (3.1 g., 0.01 mol.), 3-ethylrhodanine (1.6 g., 0.011 mol.) and triethylamine (3.1 ml.) are dissolved in ethanol (20 ml.) and heated at reflux for 10 minutes. After chilling, the solid is collected on a filter, rinsed with ethanol and dried. After one recrystallization from pyridine/methanol, the yield of purified dye is 2.2 g. (65%), m.p. 234°–235°C. with decomposition. This dye is an excellent spectral sensitizer for photographic silver halide emulsions in the minus blue region of the spectrum as set forth in Table 2 hereinafter.

EXAMPLE 4

1,3-Diethyl-5-[5,5-dimethyl-1-(1-pyrrolidinyl)-1-cyclohexen-3-ylidene]-2-thiobarbituric acid

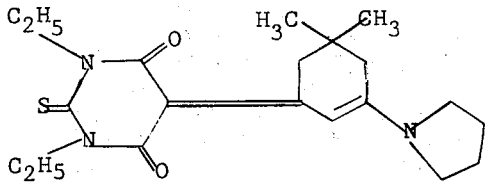

N-(3-Chloro-5,5-dimethylcyclohex-2-en-1-ylidene)-pyrrolidinium perchlorate (3.1 g., 0.01 mol.), 1,3-diethyl-2-thiobarbituric acid (2.0 g., 0.091 mol.) and triethylamine (3.1 ml.) are dissolved in ethanol (15 ml.) and heated at reflux for 10 minutes. After chilling, the crude dye is collected on a filter, rinsed with ethanol and dried. After one recrystallization from methanol, the yield of purified dye is 2.3 g. (64%), m.p. 226°–227°C. This dye is an excellent spectral sensitizer for photographic silver halide emulsions as shown in Table 2 hereinafter.

EXAMPLE 5

[5,5-Dimethyl-1-(1-pyrrolidinyl)-1-cyclohexen-3-ylidene]-(methylsulfonyl)acetonitrile

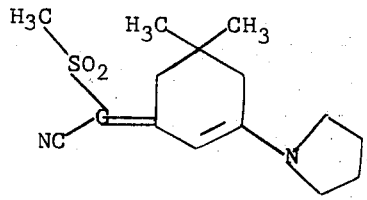

N-(3-Chloro-5,5-dimethylcyclohex-2-en-1-ylidene)-pyrrolidinium perchlorate (4.7 g., 0.015 mol.), methylsulfonylacetonitrile (1.8 g., 0.015 mol.) and triethylamine (4.6 ml.) are dissolved in ethanol (15 ml.) and heated at reflux for 5 minutes. After chilling, the crude dye is collected on a filter, washed with methanol and dried. After one recrystallization from pyridine/methanol, the yield of purified dye is 1.2 g. (27%), m.p. 260°–261°C. with decomposition. The above dye compound has excellent absorption characteristics in the ultraviolet region of the spectrum as shown in Table 1 below.

EXAMPLE 6

[5,5-Dimethyl-1-(1-pyrrolidinyl)-1-cyclohexen-3-ylidene]-(dodecylsulfonyl)acetonitrile

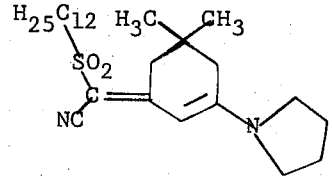

N-(3-Chloro-5,5-dimethylcyclohex-2-en-1-ylidene)-pyrrolidinium perchlorate (3.2 g.), dodecylsulfonylacetonitrile (2.7 g.) and triethylamine (3.1 ml.) are dissolved in ethanol (15 ml.) and heated at reflux for 5 minutes. After chilling, the solid is collected on a filter, washed with methanol and dried. Obtaining pure dye by recrystallization from methanol proved difficult. The product is eluted from basic alumina, using a 10% methanol-90% chloroform solvent mixture, and then recrystallized from methanol. The yield of purified dye is 0.5 g. (11%), m.p. 114°–115°C. This dye compound shows good ultraviolet absorption characteristics as indicated in the data in Table 1 below.

The light absorbing characteristics of the novel dyes of Formula I above of this invention are determined in methanol solutions of the dyes using a spectrophotometer. The values of maximum absorption peaks and the coefficient of extinction is given for each of the dyes of Examples 1, 2, 5 and 6 in Table 1 immediately below.

Table 1

| Example No. | Absorption in Methanol Solution λ Max. (nm.) | Coefficient of Extinction E × 10⁻⁴ |
|---|---|---|
| 1 | 389 | 7.0 |
| 2 | 397 | 7.8 |
| 5 | 383 | 7.3 |
| 6 | 384 | 7.0 |

EXAMPLE 7

A composition comprising gelatin, coating aids, hardeners, and the ultraviolet light-absorbing dye of Example 5, is coated above the blue sensitive layer of a multilayer reversal color film of the type described in Mannes et al. U.S. Pat. No. 2,252,718, issued Aug. 19, 1941. The resultant element has 90 mg./ft$^2$ of gelatin and 30 mg./ft$^2$ of the above dye in the overcoat. A similar element without the light-absorbing overcoat is used as a control. Spectrophotometric exposures demonstrate a significant decrease in ultraviolet sensitivity of the overcoated element of the invention relative to the control element. Practical picture tests confirm this protection. Pictures obtained with this element give a color balance similar to those obtained with the control element when the control element is exposed through a Kodak 2A Wratten filter which transmits only above about 400 nm.

Various tests of physical properties which are customarily made on coatings of this type such as vertical swell, fold, wedge brittleness, ferrotyping, gate friction, and the like give results which indicate that the control element and the overcoated element of the invention have essentially equal physical properties.

The spectral sensitizing effects in photographic emulsions of the new dyes of this invention embraced by Formula II above are illustrated by Examples 3 and 4. These are determined as follows:

The dyes dissolved in suitable solvents, are added to separate portions of a gelatin silver chlorobromide (60:40) emulsion in the concentration range of about 0.13 grams per mole of silver. After digestion at 50°C. for 10 minutes, the emulsions in each case are coated at a coverage of 432 mg. of silver per square foot and 1190 mg. of gelatin per square foot on a cellulose acetate film support. A sample of each coating is exposed on an Eastman 1B sensitometer and to a wedge spectrograph, processed in Kodak Developer D-19 of the composition:

| | |
|---|---|
| N-methyl-p-aminophenol sulfate | 2.0 g. |
| Sodium sulfite (anhydrous) | 90.0 g. |
| Hydroquinone | 8.0 g. |
| Sodium Carbonate (monohydrate) | 52.5 g. |
| Potassium bromide | 5.0 g. |
| Water to make | 1.0 liter | and then fixed, washed, and dried. The sensitometric results are recorded in the following Table 2.

Table 2

| Example No. | Conc. of Dye g./mole Silver | Sensitization Range (nm.) | Max. Sensitizing (nm.) |
|---|---|---|---|
| 3 | .13 | up to 630 | 535 |
| 4 | .13 | up to 520 | 470 |

It will be noted from the above Table 2 that the dyes of the invention defined by Formula II above provide excellent spectral sensitizers for photographic silver halide such sensitivity extending into the green to orange region of the spectrum.

In view of all of the foregoing disclosures, it will be apparent that still other dyes coming within the definitions of Formulas I and II above can be readily prepared by the selection of appropriate intermediates defined by Formulas III and IV above, and that such dyes will likewise function effectively as either ultraviolet filter dyes or as spectral sensitizers for photographic silver halide emulsions.

For example, the dyes 3-ethyl-5-[1-(di-n-propylamino)-5,5-dimethyl-1-dimethyl-1-cyclohexen-3-ylidene]rhodanine, 3-ethyl-5-[5,5-dimethyl-1-(4-ethoxycarbonylpiperazin-1-yl)-1-cyclohexen-3-ylidene]rhodanine, and 3-ethyl-5-[1-(diphenylamino)-5,5-dimethyl-1-cyclohexen-3-ylidene]rhodanine can be prepared by the method of Example 3. The dyes [5,5-dimethyl-1-(di-isobutylamino)-1-cyclohexen-3-ylidene]malononitrile and [5,5-dimethyl-1-(4-ethoxycarbonylpiperazin-1-yl)-1-cyclohexen-3-ylidene]-malononitrile can be prepared by the method of Example 1 and the dye decyl[5,5-dimethyl-1-(diphenylamino)-1-cyclohexen-3-ylidene]cyanoacetate can be prepared by the method of Example 2. Using similar procedures, the following dyes can be prepared: 3[5,5-dimethyl-1-(1-pyrrolidinyl)-1-cyclohexen-3-ylidene]-2,4-pentanedione; ethyl[5,5-dimethyl-1-(1-pyrrolidinyl)-1-cyclohexen-3-ylidene]-malonate; [5,5-dimethyl-1-(1-pyrrolidinyl)-1-cyclohexen-3-ylidene]-(phenylsulfonyl)acetonitrile; and, phenyl [5,5-dimethyl-1-(1-pyrrolidinyl)-1-cyclohexen-3-ylidene]-(phenoxysulfonyl)-acetate.

The invention has been described in considerable detail with particular reference to certain preferred embodiments thereof, however; it will be understood that variations and modifications can be effected within the spirit and scope of the invention as described hereinabove, and as defined in the appended claims.

We claim:

1. A dye selected from the group consisting of: [5,5-dimethyl-1-(1-pyrrolidinyl)-1-cyclohexen-3-ylidene]-malononitrile; decyl-[5,5-dimethyl-1-(1-pyrrolidinyl)-1-cyclohexen-3-ylidene] cyanoacetate; [5,5-dimethyl-1-(1-pyrrolidinyl)-1-cyclohexen-3-ylidene](methylsulfonyl)acetonitrile; and [5,5-dimethyl-1-(1-pyrrolidinyl)-1-cyclohexen-3-ylidene] (dodecylsulfonyl) acetonitrile.

2. A hemioxonol dye having the following formula:

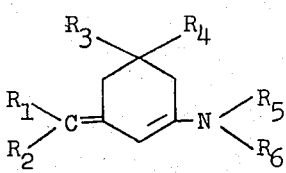

wherein $R_1$ and $R_2$ each represents a member selected from the group consisting of cyano, acetyl, propionyl, butyryl, benzoyl, furoyl, thenoyl, alkoxycarbonyl of 1 to 4 carbon atoms in the alkoxy portion, alkylsulfonyl of 1 to 4 carbon atoms, phenylsulfonyl, naphthylsulfonyl and phenoxysulfonyl, provided not more than one of $R_1$ and $R_2$ represents alkylsulfonyl, phenylsulfonyl, phenoxysulfonyl or naphthylsulfonyl; $R_3$ and $R_4$ each represents a member selected from the group consisting of a hydrogen atom or lower alkyl of 1 to 4 carbon atoms; and $R_5$ and $R_6$ taken together with the nitrogen atom to which they are attached, form pyrrolidino.

* * * * *

UNITED STATES PATENT AND TRADEMARK OFFICE
CERTIFICATE OF CORRECTION

PATENT NO. : 3,976,661
DATED : August 24, 1976
INVENTOR(S) : Leslie G. S. Brooker, Arthur Fumia, Jr., and Donald W. Heseltine It is certified that error appears in the above-identified patent and that said Letters Patent are hereby corrected as shown below:

*Column 4, line 63,

" 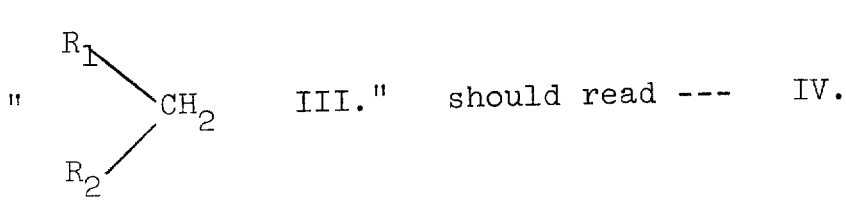 III." should read --- IV. 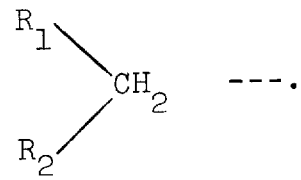 ---.

Column 14, line 36, "propylamino)-5,5-dimethyl-1-dimethyl-1-cyclohexen-" should read --- propylamino)-5,5-dimethyl-1-cyclohexen- ---.

Signed and Sealed this

First Day of March 1977

[SEAL]

Attest:

RUTH C. MASON
Attesting Officer

C. MARSHALL DANN
Commissioner of Patents and Trademarks